United States Patent
Huang et al.

(10) Patent No.: US 9,973,180 B2
(45) Date of Patent: May 15, 2018

(54) OUTPUT STAGE CIRCUIT

(71) Applicant: INDUSTRIAL TECHNOLOGY RESEARCH INSTITUTE, Chutung, Hsinchu (TW)

(72) Inventors: Yen-Chung Huang, Hsinchu (TW); Chin Hsia, Taichung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days. days.

(21) Appl. No.: 14/984,633

(22) Filed: Dec. 30, 2015

(65) Prior Publication Data
US 2017/0194953 A1 Jul. 6, 2017

(51) Int. Cl.
*H03L 5/00* (2006.01)
*H03K 5/01* (2006.01)
*H03K 19/0175* (2006.01)
*H03K 17/687* (2006.01)
*A61B 8/00* (2006.01)
(Continued)

(52) U.S. Cl.
CPC .......... *H03K 5/01* (2013.01); *A61B 8/44* (2013.01); *H03K 17/102* (2013.01); *H03K 17/162* (2013.01); *H03K 17/6872* (2013.01); *H03K 19/017509* (2013.01); *H03K 2005/00013* (2013.01)

(58) Field of Classification Search
None
See application file for complete search history.

(56) References Cited

U.S. PATENT DOCUMENTS 3,548,330 A 12/1970 Rosentein
3,898,575 A 8/1975 Koch
(Continued)

FOREIGN PATENT DOCUMENTS

CA 2093060 A1 10/1993
CN 1773768 A 5/2006
(Continued)

OTHER PUBLICATIONS

G. Stochino, "High-speed class AB voltage—current convertor with high input-output isolation", Electronics Letters Jun. 10, 2004 vol. 40 No. 12., 2 pages.
(Continued)

*Primary Examiner* — Lincoln Donovan
*Assistant Examiner* — Khareem E Almo
(74) *Attorney, Agent, or Firm* — Muncy, Geissler, Olds & Lowe, P.C.

(57) ABSTRACT

An output stage circuit comprises: a power inverter, coupled to a signal terminal; and a dynamic bias circuit, wherein the dynamic bias circuit connects between a system voltage terminal and the power inverter. The dynamic bias circuit comprises at least one Zener diode, which is configured to maintain a voltage difference between a gate terminal and a source terminal of at least one transistor of the power inverter within a first absolute value; which is configured to maintain a voltage difference between the gate terminal and a drain terminal of the at least one transistor within a second absolute value; and configured to maintain a voltage difference between the drain terminal and the source terminal of the at least one transistor within the second absolute value.

12 Claims, 4 Drawing Sheets

(51) Int. Cl.
*H03K 17/10* (2006.01)
*H03K 17/16* (2006.01)
*H03K 5/00* (2006.01)

(56) References Cited

U.S. PATENT DOCUMENTS

| | | | |
|---|---|---|---|
| 4,072,908 | A | 2/1978 | Murari et al. |
| 4,483,016 | A | 11/1984 | Hochstein et al. |
| 5,812,006 | A | 9/1998 | Teggatz et al. |
| 5,936,467 | A | 8/1999 | Strickland |
| 6,057,726 | A * | 5/2000 | Sumida .............. H03F 3/3001 326/68 |
| 6,262,601 | B1 | 7/2001 | Choe et al. |
| 6,300,837 | B1 | 10/2001 | Sowlati et al. |
| 6,437,648 | B1 | 8/2002 | Van Beylen |
| 6,559,722 | B1 | 5/2003 | Lopez et al. |
| 6,861,896 | B2 | 3/2005 | Tsividis et al. |
| 6,937,102 | B2 | 8/2005 | Lopez et al. |
| 6,956,403 | B2 | 10/2005 | Janssen |
| 7,176,760 | B2 | 2/2007 | Jones |
| 7,405,624 | B2 | 7/2008 | Franck et al. |
| 7,564,311 | B2 | 7/2009 | Rohani et al. |
| 7,920,024 | B2 | 4/2011 | Rysinski et al. |
| 8,487,687 | B2 | 7/2013 | Hsu et al. |
| 8,760,225 | B1 | 6/2014 | Wilson et al. |
| 8,829,945 | B2 | 9/2014 | Santos |
| 8,885,310 | B2 * | 11/2014 | Kandah .............. H03K 17/0826 327/434 |
| 8,890,603 | B2 | 11/2014 | Mitsuda et al. |
| 8,907,728 | B2 | 12/2014 | Watkins |
| 9,018,923 | B2 | 4/2015 | Parkhurst et al. |
| 9,099,970 | B2 | 8/2015 | Tan et al. |
| 9,450,517 | B2 * | 9/2016 | Kusama .............. H02M 7/537 |
| 9,467,138 | B2 * | 10/2016 | Osanai .............. H03K 17/567 |
| 9,531,373 | B2 * | 12/2016 | Sicard .............. H03K 17/567 |
| 2004/0066234 | A1 | 4/2004 | Luo et al. |
| 2007/0222519 | A1 | 9/2007 | Deng et al. |
| 2013/0038355 | A1 | 2/2013 | Heo |
| 2014/0266448 | A1 | 9/2014 | Cha et al. |

FOREIGN PATENT DOCUMENTS

| | | |
|---|---|---|
| CN | 101295977 A | 10/2008 |
| CN | 102957414 A | 3/2013 |
| TW | 200711293 | 3/2007 |
| TW | 200746621 | 12/2007 |
| TW | 200849808 A | 12/2008 |
| TW | 201015846 A | 4/2010 |
| TW | 201203843 A | 1/2012 |
| TW | 201429156 A | 7/2014 |
| TW | I499792 B | 9/2015 |

OTHER PUBLICATIONS

D. Zhao, M. T. Tan, H. K. Cha, J. Qu, Y. Mei, H.Yu, A. Basu, M. Je, "High-voltage Pulser for Ultrasound Medical Imaging Applications", 2011 International Symposium on Integrated Circuits, pp. 408-411.
U. Guler and A. Bozkurt, "A Low-Noise Front-End Circuit for 2D cMUT Arrays", 2006 IEEE Ultrasonics Symposium, pp. 689-692.
Chin Hsia, Zhu, A., Yan, J.J., Draxler, P., Kimball, D.F, Lanfranco, S., Asbeck, P.M., "Digitally assisted dual-switch high-efficiency envelope amplifier for envelope-tracking base-station power amplifiers", IEEE Transactions on Microwave Theory and Techniques, vol. 59, Iss. 11, Nov. 2011, pp. 2943-2952.
J. Jeong; Kimball, D.F.; M. Kwak, Chin Hsia; Draxler, P.; Asbeck, P.M, "Modeling and Design of RF Amplifiers for Envelope Tracking WCDMA Base-Station Applications", IEEE Transactions on Microwave Theory and Techniques vol. 57, Iss. 9, 2009, pp. 2148-2159.
X. Xu, J. T. Yen, and K. K. Shung, "A Low-Cost Bipolar Pulse Generator for High-Frequency Ultrasound Applications", IEEE Transactions Ultrasonics, Ferroelectrics, and Frequency control, vol. 54, No. 2, Feb. 2007.
K. Chen, H. S Lee, A. P. Chandrakasan, and C. G. Sodini, "Ultrasonic Imaging Transceiver Design for CMUT: A Three-Level 30-Vpp Pulse-Shaping Pulser With Improved Efficiency and Noise-Optimized Receiver", IEEE Journal of Solid-State Circuits, vol. 48, No. 11, Nov. 2013, pp. 2734-2745.
J. Jeong, et al., "High-Efficiency WCDMA Envelope Tracking Base-Station Amplifier Implemented With GaAs HVHBTs", IEEE Journal of Solid-State Circuits, vol. 44, No. 10, Oct. 2009, pp. 2629-2639.
J. Jeong; Kimball, D.; M. Kwak ; Draxler, P.; Chin Hsia; Steinbeiser, C. ; Landon, T. ; Krutko, O. ; Larson, L.E. ; Asbeck, P.M., "High-Efficiency WCDMA Envelope Tracking Base-Station Amplifier Implemented With GaAs HVHBTs", IEEE Journal of Solid-State Circuits, vol. 44, Iss. 10, 2009, pp. 2629-2639.
J. A. Brown and G. R. Lockwood, "A Low-Cost, High-Performance Pulse Generator for Ultrasound Imaging", IEEE Transactions on Ultrasonics, Ferroelectrics, and Frequency Control, vol. 49, No. 6, Jun. 2002, pp. 848-851.
Dongning Zhao ; Meng Tong Tan ; Hyouk-Kyu Cha ; Jinli Qu ; Yan Mei ; Hao Yu ; Basu, A. ; Minkyu Je "High-voltage pulser for ultrasound medical imaging applications", Integrated Circuits (ISIC), 2011 13th International Symposium on Digital Object Identifier: 10.1109/ISICir.2011.6131983 Publication Year: 2011, pp. 408-411.
H.K. Cha, D. Zhao, J. H. Cheong, and B. Guo, "A CMOS High-Voltage Transmitter IC for Ultrasound Medical Imaging Applications", IEEE Transactions on Circuits and Systems—II: Express Briefs, vol. 60, No. 6, Jun. 2013, pp. 316-320.
C. T. Chuang, "Advanced Bipolar Circuits—A Perspective", VLSI-TSA, 1991, pp. 394-397.
Frederick H. Raab, "Class-D Power Amplifier with RF Pulse-Width Modulation", IEEE IMS-Digest 2010, pp. 94-97.
D. Kimball, J. Jeong, Chin Hsia, P. Draxler, S. Lanfranco, W. Nagy, K. Linthicum, L. E. Larson and P M. Asbeck, "High-Efficiency Envelope-Tracking W-CDMA Base-Station Amplifier Using GaN HFETs", IEEE Transactions on Microwave Theory and Techniques, vol. 54, Iss. 11, 2006, pp. 3848-3856.
G. Gurun, P. Hasler, and F. L. Degertekin, "A 1.5-mm Diameter Single-Chip CMOS Front-End System with Transmit-Receive Capability for CMUT on CMOS Forward-Looking IVUS", 2011 IEEE International Ultrasonics Symposium Proceedings, pp. 478-481.
Chin Hsia, Yen-Chung Huang and Chih-Wen Lu, "Single-chip Ultra High Slew-rate Pulse Generator for Ultrasound Scanner Applications", 2013 IEEE Joint UFFC, EFTF and PFM Symposium, pp. 1556-1559.
E. Botti, T. Mandrini, and F. Stefani, "A High-Efficiency 4x20 W Monolithic Audio Amplifier for Automobile Radios Using a Complementary D-MOS BCD Technology", IEEE Journal of Solid-State Circuits, vol. 31, No. 12, Dec. 1996, pp. 1895-1901.
J. Yan, Chin Hsia, D. Kimball, P. Asbeck, "Design of a 4W Envelope Tracking Power Amplifier with More Than One Octave Carrier Bandwidth", IEEE Journal of Solid-State Circuits, vol. 47, No. 10, 2012, pp. 2298-2308.
L. R. Cenkeramaddi, A. Bozkurt, F. Y. Yamaner and T. Ytterda, "A Low Noise Capacitive Feedback Analog Front-end for CMUTs in Intra Vascular Ultrasound Imaging", 2007 IEEE Ultrasonics Symposium, pp. 2143-2146.
Johan Borg, and Jonny Johansson, "An Ultrasonic Transducer Interface IC With Integrated Push-Pull 40 Vpp, 400 mA Current Output, 8-bit DAC and Integrated HV Multiplexer", IEEE Journal of Solid-State Circuits, vol. 46, No. 2, Feb. 2011, pp. 475-484.

* cited by examiner

OUTPUT STAGE CIRCUIT

TECHNICAL FIELD

The technical field relates to an output stage circuit.

BACKGROUND

Regarding designs of output stage circuits, most of circuitry adopts a push-pull scheme for purposes of high speed and high efficiency. Concerning one of advantages of the push-pull scheme, the push-pull scheme can achieve almost a rail-to-rail output. Therefore, the push-pull scheme has high efficiency and is easily integrated into IC (integrated circuit). A significant trend throughout integrated circuit (IC) development is the downsizing of IC components. As the size reduces, the performance requirements become more stringent. Also, as devices continue to shrink in size, the channel region continues to shrink as well. For metal-oxide-semiconductor field effect transistors (MOSFETs), increased performance requirements have generally been met by aggressively scaling the length of the channel region. However, such a short channel length or scaling down faces problems of decreasing breakdown voltages. Ranges of output voltages are limited to characters of processing or physical restriction of devices. It becomes harder to utilize devices having low breakdown voltages into systems where output voltages are much higher than breakdown voltages of each devices.

SUMMARY

An embodiment of the disclosure relates to an output stage circuit. The output stage circuit comprises: a power inverter, coupled to a signal terminal; and a dynamic bias circuit, wherein the dynamic bias circuit connects between a system voltage terminal and the power inverter. The dynamic bias circuit comprises at least one Zener diode, which is configured to maintain a voltage difference between a gate terminal and a source terminal of at least one transistor of the power inverter within a first absolute value. The at least one Zener diode is also configured to maintain a voltage difference between the gate terminal and a drain terminal of the at least one transistor within a second absolute value. The at least one Zener diode is also configured to maintain a voltage difference between the drain terminal and the source terminal of the at least one transistor within the second absolute value.

An embodiment of the disclosure relates to a signal processing method of output stage circuit. The method comprises: receiving a first level signal; maintaining a voltage difference between a gate terminal and a source terminal of a p-type transistor, wherein the voltage difference enables the p-type transistor work at a linear region when turning on; outputting a highest system voltage; receiving a second level signal; maintaining a voltage difference between a gate terminal and a source terminal of an n-type transistor, wherein the voltage difference enables the n-type transistor work at a linear region when turning on; and outputting a lowest system voltage.

The foregoing will become better understood from a careful reading of a detailed description provided herein below with appropriate reference to the accompanying drawings.

BRIEF DESCRIPTION OF THE DRAWINGS

Aspects of the present disclosure are described with reference to the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION OF DISCLOSED EMBODIMENTS

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

An embodiment of the present disclosure discloses an output stage circuit, which is not restricted by breakdown voltages of each devices or transistors. In the integrated circuit industry, semiconductor devices continue to scale down by advance processes. For example, channels of the semiconductor devices are shortened so that speed of switch becomes faster. However, the scaling down of devices causes the semiconductor devices hard to endure or tolerate operations of high voltage or high current. For example, in the field of ultrasonic wave, a high voltage pulser or a high pulse generator at an output stage circuit is utilized to drive transducers. If a high voltage output circuit is tried to be implemented by integrated circuit processes, a specific design for the output stage circuit is adopted to overcome low breakdown voltages of each semiconductor devices. In general, the high voltage pulser or the high pulse generator of the output stage circuit is limited to breakdown voltages of each semiconductor devices. For example, a 60V transistor integrated in the output stage circuit outputs a 0-60V or ±30V swing. The present disclosure provides an output stage circuit, which is not restricted by breakdown voltages of each devices or transistors. Low-voltage semiconductor devices are collected and designed to achieve a large swing of output voltage.

Figure 1:
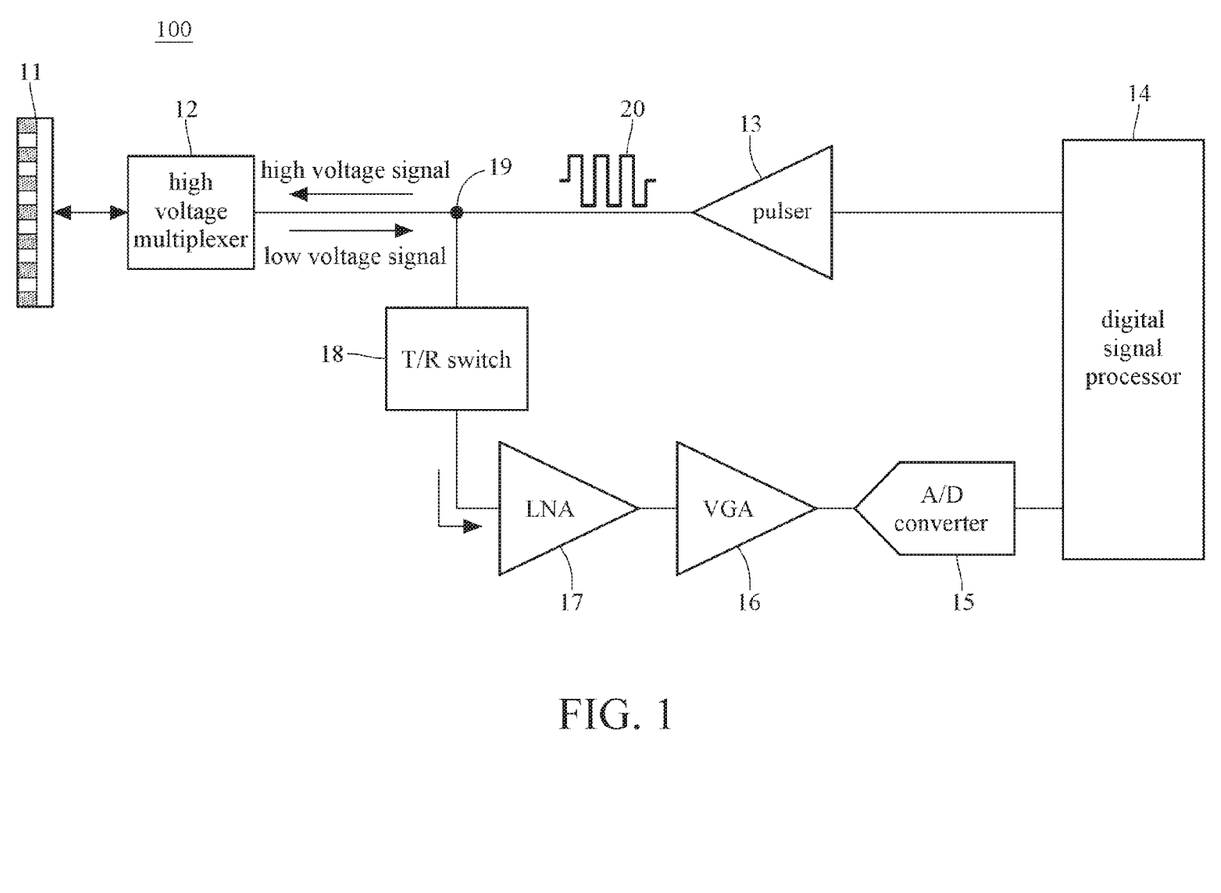
FIG. 1 is a diagram illustrating an ultrasonic wave system in accordance with an embodiment of the present disclosure.

FIG. 1 is a diagram illustrating an ultrasonic wave system 100 in accordance with an embodiment of the present disclosure. The ultrasonic wave system 100 comprises a transducer array 11, a high voltage multiplexer 12, a pulser 13, a digital signal processor 14, a A/D converter 15, a variable gain amplifier (VGA) 16, a low-noise amplifier (LNA) 17, and a T/R switch 18. The transducer array 11 electrically connects to the high voltage multiplexer 12. The high voltage multiplexer 12, an output terminal of the pulser 13, and the T/R switch 18 connect to a node 19. The T/R switch 18 connects to the LNA 17. The LNA 17 connects to the VGA 16. The VGA 16 connects to the A/D converter 15. The LNA 17 is located between the T/R switch 18 and the VGA 16. The VGA 16 is located between the A/D converter 15 and the LNA 17. The A/D converter 15 is located between the VGA 16 and the digital signal processor 14. The digital signal processor 14 simultaneously connects to the pulser 13 and the A/D converter 15.

The digital signal processor 14 is able to process all digital signals of the ultrasonic wave system 100. The digital signal processor 14 instructs the pulser 13 to emit a high voltage signal 20. By channel control of the T/R switch 18, the high voltage signal 20 is transmitted though the node 19 to the high voltage multiplexer 12. The high voltage multiplexer 12 guides switching of multiple signal channels by control of selection lines. The high voltage signal 20 is thus transmitted to the transducer array 11. The transducer array 11 is capable of transforming electric signals into ultrasonic wave or other physical signals, such as light or heat. In addition, the ultrasonic wave is emitted to sensed objects, for example, human or animals. The sensed objects receive the ultrasonic wave and generate reflected ultrasonic wave or other physical signals. The transducer array 11 senses the reflected ultrasonic wave and analyzes its physiology information. Further, the reflected ultrasonic wave is transformed into a low voltage signal by the transducer array 11. The low voltage signal, which brings the physiology information, is transmitted to the node 19 by channel switching of the high voltage multiplexer 12. Further, the low voltage signal is transmitted to the LNA 17 by the T/R switch 18. The LNA 17 amplifies the low voltage signal so as to be compatible for signal processing of next stage. In addition, the low voltage signal is also processed by the A/D converter 15 and the VGA 16. The digital signal processor 14 thus receives and analyzes the low voltage signal, which brings the physiology information. The VGA 16 is able to adjust voltage gain of received signals so that different stages of circuit are compatible. The A/D converter 15 is able to transform analog signals into digital signals.

The present disclosure emphasizes on an output stage circuit of the pulser 13. The purpose of the present disclosure is to achieve a high voltage output and a large output swing by using integrated circuit processes or transistors with low breakdown voltages. Details of the output stage circuit are as follows.

Figure 2:
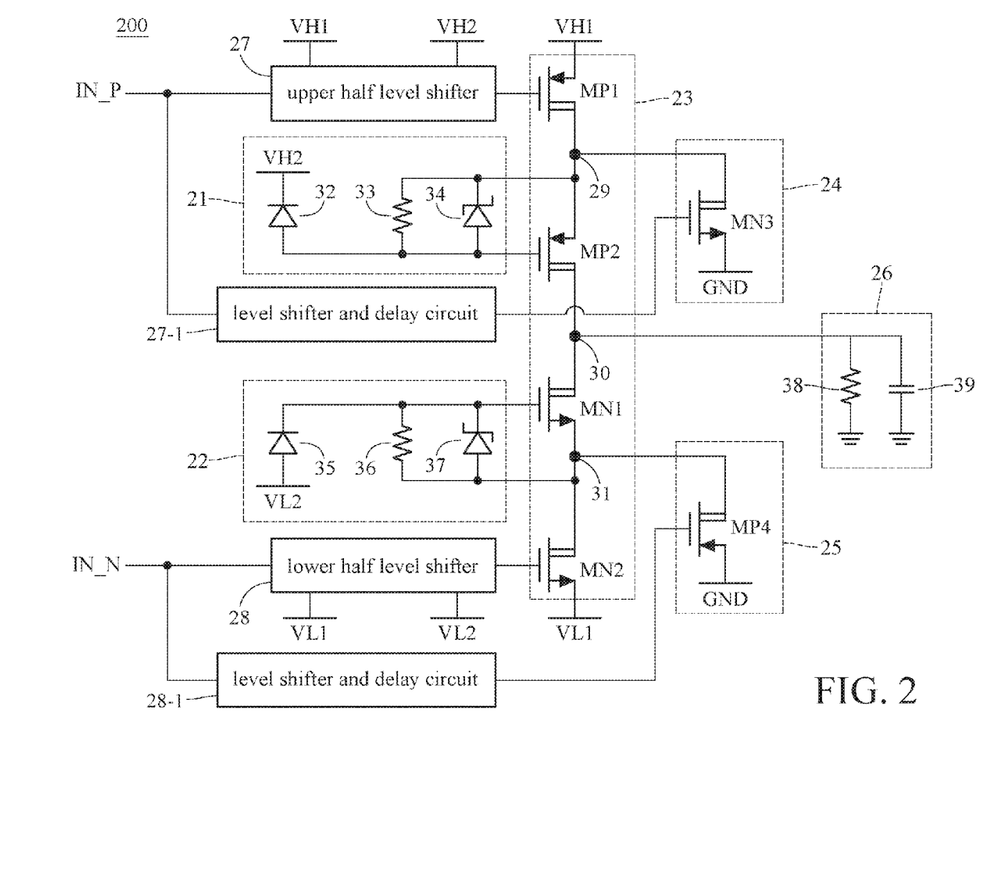
FIG. 2 is a diagram illustrating an output stage circuit in accordance with an embodiment of the present disclosure.

FIG. 2 is a diagram illustrating an output stage circuit 200 in accordance with an embodiment of the present disclosure. The output stage circuit 200 comprises an upper half dynamic bias circuit 21, a lower half dynamic bias circuit 22, a power inverter 23, an upper half protection circuit 24, a lower half protection circuit 25, a load 26, an upper half level shifter 27, a lower half level shifter 28, a first high voltage terminal VH1, a second high voltage terminal VH2, a first low voltage terminal VL1, a second low voltage terminal VL2, a level shifter and delay circuit 27-1, and a level shifter and delay circuit 28-1. The first high voltage terminal VH1, the second high voltage terminal VH2, the first low voltage terminal VL1, and the second low voltage terminal VL2 are called as system voltage terminals.

The power inverter 23 comprises p-type transistors MP1 and MP2, and n-type transistors MN1 and MN2. The p-type transistors MP1 and MP2, and n-type transistors MN1 and MN2 are semiconductor devices, such as power metal oxide semiconductor field effect transistors (power MOSFETs). A gate terminal of the p-type transistor MP1 connects to the upper half level shifter 27. A source terminal of the p-type transistor MP1 connects to the first high voltage terminal VH1. A drain terminal of the p-type transistor MP1 connects to a source terminal of the p-type transistor MP2. A gate terminal and a source terminal of the p-type transistor MP2 both connect to the upper half dynamic bias circuit 21. A drain terminal of the p-type transistor MP2 connects to a drain terminal of the n-type transistor MN1. A gate terminal and a source terminal of the n-type transistor MN1 both connect to the lower half dynamic bias circuit 22. The source terminal of the n-type transistor MN1 also connects to a drain terminal of the n-type transistor MN2. A gate terminal of the n-type transistor MN2 connects to the lower half level shifter 28. A source terminal of the n-type transistor MN2 connects to the first low voltage terminal VL1. Specially, a node 29 is located between the p-type transistors MP1 and MP2. The node 29 connects to the drain terminal of the p-type transistor MP1, the source terminal of the p-type transistor MP2, a port of the upper half dynamic bias circuit 21, and a port of the upper half protection circuit 24. A node 30 is located between the p-type transistor MP2 and the n-type transistor MN1. The node 30 connects to the drain terminal of the p-type transistor MP2, the drain terminal of the n-type transistor MN1, and a port of the load 26. A node 31 is located between the n-type transistors MN1 and MN2. The node 31 connects to the source terminal of the n-type transistor MN1, the drain terminal of the n-type transistor MN2, a port of the lower half dynamic bias circuit 22, and a port of the lower half protection circuit 25.

The upper half level shifter 27 respectively connects to the first high voltage terminal VH1, the second high voltage terminal VH2, a signal input terminal IN_P, and the gate terminal of the p-type transistor MP1. The lower half level shifter 28 respectively connects to the first low voltage terminal VL1, the second low voltage terminal VL2, a signal input terminal IN_N, and the gate terminal of the n-type transistor MN2. The upper half level shifter 27 may comprise a plurality of p-type transistors or n-type transistors, wherein the upper half level shifter 27 boosts signals coming from the signal input terminal IN_P. Further, the upper half level shifter 27 outputs a voltage with a larger absolute value, such as a voltage of the first high voltage terminal VH1 or the second high voltage terminal VH2. The lower half level shifter 28 may comprise a plurality of p-type transistors or n-type transistors, wherein the lower half level shifter 28 steps down signals coming from the signal input terminal IN_N. Further, the lower half level shifter 28 outputs a voltage with a larger absolute value, such as a voltage of the first low voltage terminal VL1 or the second low voltage terminal VL2.

The upper half dynamic bias circuit 21 comprises a diode 32, a resistance 33, and a Zener diode 34. The diode 32 connects between the second high voltage terminal VH2 and the gate terminal of the p-type transistor MP2. An anode of the diode 32 connects to the gate terminal of the p-type transistor MP2. A cathode of the diode 32 connects to the second high voltage terminal VH2. The Zener diode 34 bridges between the node 29 and the gate terminal of the p-type transistor MP2. In other words, the Zener diode 34 bridges between the source terminal and the gate terminal of the p-type transistor MP2. Specifically, an anode of the Zener diode 34 connects to the gate terminal of the p-type transistor MP2. A cathode of the Zener diode 34 connects to the source terminal of the p-type transistor MP2. The resistance 33 and the Zener diode 34 are implemented as a shunt connection, that is, the resistance 33 connects to the Zener diode 34 in parallel. An end of the resistance 33 connects to the source terminal of the p-type transistor MP2. The other end of the resistance 33 connects to the gate terminal of the p-type transistor MP2.

The lower half dynamic bias circuit 22 comprises a diode 35, a resistance 36, and a Zener diode 37. The diode 35 connects between the second low voltage terminal VL2 and the gate terminal of the n-type transistor MN1. A cathode of the diode 35 connects to the gate terminal of the n-type transistor MN1. An anode of the diode 35 connects to the second low voltage terminal VL2. The Zener diode 37 bridges between the node 31 and the gate terminal of the n-type transistor MN1. In other words, the Zener diode 37 bridges between the source terminal and the gate terminal of the n-type transistor MN1. Specifically, an anode of the Zener diode 37 connects to the source terminal of the n-type transistor MN1. A cathode of the Zener diode 37 connects to the gate terminal of the n-type transistor MN1. The resistance 36 and the Zener diode 37 are implemented as a shunt connection. An end of the resistance 36 connects to the source terminal of the n-type transistor MN1. The other end of the resistance 36 connects to the gate terminal of the n-type transistor MN1.

The upper half protection circuit 24 comprises an n-type transistor MN3, wherein a gate terminal of the n-type transistor MN3 connects to the level shifter and delay circuit 27-1. The n-type transistor MN3 indirectly receives signals coming from the signal input terminal IN_P, wherein the signal input terminal IN_P has at least two level signals such as different voltages. A drain terminal of the n-type transistor MN3 connects to the node 29. A source terminal of the n-type transistor MN3 is grounded.

The lower half protection circuit 25 comprises a p-type transistor MP4, wherein a gate terminal of the p-type transistor MP4 connects to a level shifter and delay circuit 28-1. The p-type transistor MP4 indirectly receives signals coming from the signal input terminal IN_N, wherein the signal input terminal IN_N has at least two level signals such as different voltages. A drain terminal of the p-type transistor MP4 connects to the node 31. A source terminal of the p-type transistor MP4 is grounded.

In this embodiment, the load 26 comprises a resistance 38 and a capacitance 39. The load 26 symbolizes an external equipment, such as a transducer. The load 26 is not limited to this embodiment.

In this embodiment, operation of the output stage circuit 200 can be divided to a state of positive half wave and a state of negative half wave. The state of positive half wave corresponds to a turn-on of upper half transistors of the power inverter 23. The state of negative half wave corresponds to a turn-on of lower half transistors of the power inverter 23. At the state of positive half wave, the p-type transistors MP1 and MP2 turn on; and the n-type transistors MN1 and MN2 turn off. A voltage of the first high voltage terminal VH1 is higher than a voltage of the second high voltage terminal VH2, for example, VH1=60V and VH2=55V. Both of the first high voltage terminal VH1 and the second high voltage terminal VH2 provides positive voltages. The upper half level shifter 27 receives signals coming from the signal input terminal IN_P and outputs the voltage of the second high voltage terminal VH2 to the p-type transistor MP1. As such, the p-type transistor MP1 turns on. A voltage of the node 29 is VH1-$V_{SD}$, wherein the $V_{SD}$ refers to a voltage difference between the source terminal and the drain terminal of the p-type transistor MP1. Since the second high voltage terminal VH2 provides a lower voltage than that of the node 29, the Zener diode 34 turns on at a reverse bias. A voltage of an anode of the Zener diode 34 is (VH1-$V_{SD}$-$V_{ZENER}$), wherein the $V_{ZENER}$ refers to a voltage difference between the anode and the cathode of the Zener diode 34. Further, deriving from the second high voltage terminal VH2, the diode 32 turns on so that a voltage of the anode of the Zener diode 34 is (VH2+$V_{DIODE}$). At the anode of the Zener diode 34, it satisfies an equation (VH2+$V_{DIODE}$)=(VH1-$V_{SD}$-$V_{ZENER}$). Since the Zener diode 34 and the resistance 33 are performed as a shunt connection, a voltage difference between two ends of the resistance 33 is equal to $V_{ZENER}$. Specially, by using the shunt connection of the Zener diode 34 and the resistance 33, which bridges across the source terminal and the gate terminal of the p-type transistor MP2, a voltage difference between the gate terminal and the source terminal of the p-type transistor MP2 is maintained within an absolute value. The absolute value is equivalence with an operating voltage range at a reverse bias of the Zener diode 34. As such, the absolute value presents a dynamic voltage difference, wherein the absolute value ranges from a breakdown voltage of the reverse bias to 0V. Therefore, the dynamic voltage difference generates a dynamic bias to the gate terminal of the p-type transistor MP2. In addition, a voltage difference between the gate terminal and the source terminal of the p-type transistor MP2 is equal to the voltage difference between the anode and the cathode of the Zener diode 34. By using a voltage restriction of the Zener diode 34, the p-type transistor MP2 works at a linear region (a triode region) when turning on. The Zener diode 34 avoids the p-type transistor MP2 work at a breakdown region when turning on. Therefore, the p-type transistor MP2 works at a linear region when turning on. A voltage at the node 30 is VH1-$2V_{SD}$, wherein the voltage at the node 30 is slightly lower than the first high voltage terminal VH1. The load 26 thus receives the voltage at the node 30, VH1-$2V_{SD}$. Furthermore, the upper half protection circuit 24 turns off; and the lower half protection circuit 25 turns on so that the node 31 is grounded. The lower half protection circuit 25 prevents the n-type transistors MN1 and MN2 from transient over voltage. In other words, the lower half protection circuit 25 guides the transient over voltage. In addition, regarding the n-type transistor MN1, the node 31 is grounded so as to ensure a voltage difference between the drain terminal and the source terminal of the n-type transistor MN1 within an absolute value. Since the Zener diode 37 is at a forward bias, the gate terminal of the n-type transistor MN1 rapidly becomes -$V_{DIODE}$. A voltage difference between the gate terminal and the source terminal of the n-type transistor MN1 is thus maintained within an absolute value. Regarding the n-type transistor MN2, the node 31 is grounded so as to ensure a voltage difference between the drain terminal and the source terminal of the n-type transistor MN2 within an absolute value. In addition, a voltage difference between the gate terminal and the source terminal of the n-type transistor MN2 is also maintained within an absolute value.

At the state of negative half wave, the p-type transistors MP1 and MP2 turn off; and the n-type transistors MN1 and MN2 turn on. An absolute voltage value of the first low voltage terminal VL1 is higher than an absolute voltage value of the second low voltage terminal VL2. Both of the first low voltage terminal VL1 and the second low voltage terminal VL2 provides negative voltages. For example, VL1=-60V; VL2=-55V; and |VL1|>|VL2|. The lower half level shifter 28 receives signals coming from the signal input terminal IN_N and outputs the voltage of the second low voltage terminal VL2 to the n-type transistor MN2. As such, the n-type transistor MN2 turns on. A voltage of the node 31 is (VL1+$V_{DS}$), wherein the $V_{DS}$ refers to a voltage difference between the drain terminal and the source terminal of the n-type transistor MN2. The voltages of the node 31 and the second low voltage terminal VL2 are negative values. In comparison, the second low voltage terminal VL2 has a higher voltage than that of the node 31. The voltage of the node 31 is equivalence with an anode voltage of the Zener diode 37. Thus, the Zener diode 37 turns on at a reverse bias. A voltage of a cathode of the Zener diode 37 is (VL1+$V_{DS}$+$V_{ZENER}$), wherein the $V_{ZENER}$ refers to a voltage difference between the anode and the cathode of the Zener diode 37.

Further, deriving from the second low voltage terminal VL2, the diode 35 turns on so that a voltage of the cathode of the Zener diode 37 is (VL2−$V_{DIODE}$). At the cathode of the Zener diode 37, it satisfies an equation (VL2−$V_{DIODE}$)=(VL1+$V_{DS}$+$V_{ZENER}$). Since the Zener diode 37 and the resistance 36 are performed as a shunt connection, a voltage difference between two ends of the resistance 36 is equal to $V_{ZENER}$. Specially, by using the shunt connection of the Zener diode 37 and the resistance 36, which bridges across the source terminal and the gate terminal of the n-type transistor MN1, a voltage difference between the gate terminal and the source terminal of the n-type transistor MN1 is maintained within an absolute value. The absolute value is equivalence with an operating voltage range at a reverse bias of the Zener diode 37. As such, the absolute value presents a dynamic voltage difference, wherein the absolute value ranges from a breakdown voltage of the reverse bias to 0V. Therefore, the dynamic voltage difference generates a dynamic bias to the gate terminal of the n-type transistor MN1. In addition, a voltage difference between the gate terminal and the source terminal of the n-type transistor MN1 is equal to the voltage difference between the anode and the cathode of the Zener diode 37. By using a voltage restriction of the Zener diode 37, the n-type transistor MN1 works at a linear region (a triode region) when turning on. The Zener diode 37 avoids the n-type transistor MN1 work at a breakdown region when turning on. Therefore, the n-type transistor MN1 works at a linear region when turning on. A voltage at the node 30 is VL1+2$V_{DS}$, wherein the voltage at the node 30 is a negative value and slightly higher than that of the first low voltage terminal VL1. The load 26 thus receives the voltage at the node 30, VL1+2$V_{DS}$.

Furthermore, the upper half protection circuit 24 turns on so that the node 29 is grounded; and the lower half protection circuit 25 turns off. The upper half protection circuit 24 prevents the p-type transistors MP1 and MP2 from transient over voltage. In other words, the upper half protection circuit 24 guides the transient over voltage. In addition, regarding the p-type transistor MP2, the node 29 is grounded so as to ensure a voltage difference between the drain terminal and the source terminal of the p-type transistor MP2 within an absolute value. Since the Zener diode 34 is at a forward bias, the gate terminal of the p-type transistor MP2 rapidly becomes +$V_{DIODE}$. A voltage difference between the gate terminal and the source terminal of the p-type transistor MP2 is thus maintained within an absolute value. Regarding the p-type transistor MP1, the node 29 is grounded so as to ensure a voltage difference between the drain terminal and the source terminal of the p-type transistor MP1 within an absolute value. In addition, a voltage difference between the gate terminal and the drain terminal of the p-type transistor MP1 is also maintained within an absolute value. That is, by using the Zener diode 34 and the resistance 33, the voltage difference between the gate terminal and the source terminal of the p-type transistor MP2 is limited within an absolute value, for example, $V_{SG}$≤|5V|. The voltage difference between the gate terminal and the drain terminal of the p-type transistor MP2 is limited within an absolute value, for example, $V_{GD}$≤|60V|. The voltage difference between the source terminal and the drain terminal of the p-type transistor MP2 is limited within an absolute value, for example, $V_{SD}$≤|60V|. In this embodiment, the absolute value for $V_{GD}$ is equivalence with that of $V_{SD}$. In another embodiment, absolute values for $V_{SG}$, $V_{GD}$, and $V_{SD}$ are different by adjustment of the Zener diode 37 and the resistance 36.

By using the restriction of the Zener diode 37 and the resistance 36, the p-type transistor MP2 and the n-type transistor MN1 will certainly operate at a linear region when turning on. An output swing of the node 30 is up to (VH1−2$V_{SD}$)~(VL1+2$V_{DS}$), which is close to a voltage difference between the highest voltage and the lowest voltage of the system. Therefore, this embodiment achieves a large swing of output voltage by using power semiconductor devices having low-voltage tolerance. The large swing of output voltages are provided for high voltage or high power equipment, such as ultrasonic wave transducers or logic inverters.

Figure 3:
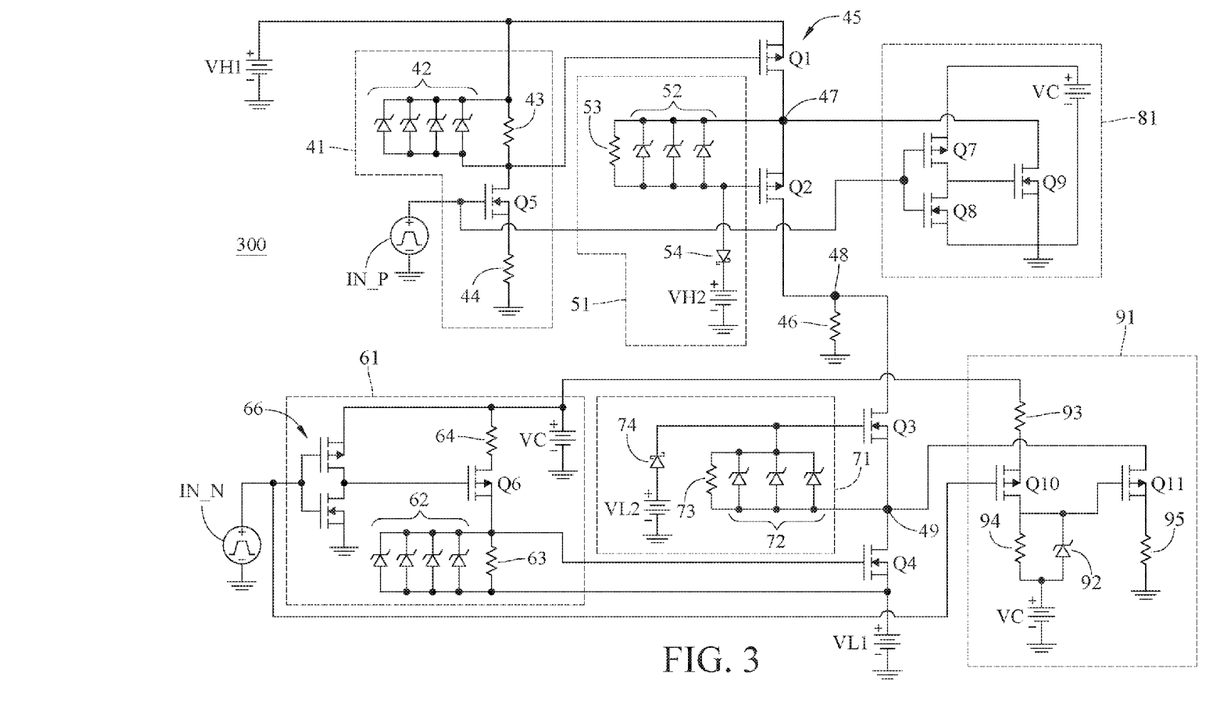
FIG. 3 is a diagram illustrating an output stage circuit in accordance with an embodiment of the present disclosure.

FIG. 3 is a diagram illustrating an output stage circuit 300 in accordance with an embodiment of the present disclosure. The output stage circuit 300 comprises an upper half dynamic bias circuit 51, a lower half dynamic bias circuit 71, a power inverter 45, an upper half protection circuit 81, a lower half protection circuit 91, a load 46, an upper half level shifter 41, a lower half level shifter 61, a first high voltage terminal VH1, a second high voltage terminal VH2, a first low voltage terminal VL1, and a second low voltage terminal VL2.

The power inverter 45 comprises p-type transistors Q1 and Q2; and n-type transistors Q3 and Q4. The p-type transistors Q1 and Q2 and the n-type transistors Q3 and Q4 are semiconductor devices, such as power metal oxide semiconductor field effect transistors (power MOSFETs), channel enhanced MOSFETs, channel depleted MOSFETs, or other suitable devices. A gate terminal of the p-type transistor Q1 connects to the upper half level shifter 41. A source terminal of the p-type transistor Q1 connects to the first high voltage terminal VH1. A drain terminal of the p-type transistor Q1 connects to a source terminal of the p-type transistor Q2. A gate terminal and the source terminal of the p-type transistor Q2 respectively connects to the upper half dynamic bias circuit 51. A drain terminal of the p-type transistor Q2 connects to a drain terminal of the n-type transistor Q3. A gate terminal and a source terminal of the n-type transistor Q3 respectively connects to the lower half dynamic bias circuit 71. The source terminal of the n-type transistor Q3 also connects to a drain terminal of the n-type transistor Q4. A gate terminal and a source terminal of the n-type transistor Q4 respectively connects to the lower half level shifter 61. In addition, the source terminal of the n-type transistor Q4 connects to the first low voltage terminal VL1. Specially, a node 47 is located between the p-type transistors Q1 and Q2. The node 47 collects and connects the drain terminal of the p-type transistor Q1, the source terminal of the p-type transistor Q2, a port of the upper half dynamic bias circuit 51, and a port of the upper half protection circuit 81 together. A node 48 is located between the p-type transistor Q2 and the n-type transistor Q3. The node 48 also collects and connects the drain terminal of the p-type transistor Q2, the drain terminal of the n-type transistor Q3, and a port of the load 46 together. A node 49 is located between the n-type transistors Q3 and Q4. The node 49 collects and connects the source terminal of the n-type transistor Q3, the drain terminal of the n-type transistor Q4, a port of the lower half dynamic bias circuit 71, and a port of the lower half protection circuit 91 together.

In this embodiment, the upper half level shifter 41 comprises a plurality of Zener diode 42, resistances 43 and 44, and n-type transistor Q5. The plurality of Zener diode 42 and the resistance 43 are implemented as a shunt connection. Anodes of each Zener diode 42 all connects to the gate terminal of the p-type transistor Q1 and a drain terminal of the n-type transistor Q5. Cathodes of each Zener diode 42 connects to the first high voltage terminal VH1. The gate terminal of the n-type transistor Q5 connects to a signal input terminal IN_P. Another end of the signal input terminal IN_P is grounded. The source terminal of the n-type transistor Q5 connects to the resistance 44, wherein another end of the resistance 44 is grounded.

The lower half level shifter 61 comprises a plurality of Zener diodes 62, a resistance 63, a p-type transistor Q6, a resistance 64, a constant voltage terminal Vc, and an inverter 66. The plurality of Zener diodes 62 and the resistance 63 are implemented as a shunt connection. Anodes of each Zener diodes 62 all connects to the source terminal of the n-type transistor Q4. Cathodes of each Zener diodes 62 connects to the gate terminal of the n-type transistor Q4 and a drain terminal of the p-type transistor Q6. The inverter 66 is performed by an n-type transistor and a p-type transistor. An end of the inverter 66 connects to the constant voltage terminal Vc. Another end of the inverter 66 is grounded. A gate terminal of the p-type transistor Q6 connects to an output terminal of the inverter 66. A signal input terminal IN_N connects to an input terminal of the inverter 66. A source terminal of the p-type transistor Q6 connects to the resistance 64, wherein another end of the resistance 64 connects to the constant voltage terminal Vc. The constant voltage terminal Vc is configured as a drive voltage for driving the p-type transistor Q6, for example, 5V. The constant voltage terminal Vc is much smaller than the first high voltage terminal VH1 or the second high voltage terminal VH2.

The upper half dynamic bias circuit 51 comprises three Zener diodes 52, a resistance 53, a Schottky diode 54, and the second high voltage terminal VH2. The Schottky diode 54 connects between the second high voltage terminal VH2 and the gate terminal of the p-type transistor Q2. An anode of the Schottky diode 54 connects to the gate terminal of the p-type transistor Q2. A cathode of the Schottky diode 54 connects to the second high voltage terminal VH2. The three Zener diodes 52 are implemented as a shunt connection. Each Zener diodes 52 bridges between the node 47 and the gate terminal of the p-type transistor Q2. In other words, each Zener diodes 52 bridges between the source terminal and the gate terminal of the p-type transistor Q2. Specifically, anodes of each Zener diodes 52 connect to the gate terminal of the p-type transistor Q2. Cathodes of each Zener diodes 52 connect to the source terminal of the p-type transistor Q2. An end of the resistance 53 connects to the source terminal of p-type transistor Q2. Another end of the resistance 53 connects to the gate terminal of the p-type transistor Q2.

The lower half dynamic bias circuit 71 comprises three Zener diodes 72, a resistance 73, a Schottky diode 74, and the second low voltage terminal VL2. The Schottky diode 74 connects between the second low voltage terminal VL2 and the gate terminal of the n-type transistor Q3. A cathode of the Schottky diode 74 connects to the gate terminal of the n-type transistor Q3. An anode of the Schottky diode 74 connects to the second low voltage terminal VL2. Each Zener diodes 72 bridges between the node 49 and the gate terminal of the n-type transistor Q3. In other words, each Zener diodes 72 bridges between the gate terminal and the source terminal of the n-type transistor Q3. Specifically, anodes of each Zener diodes 72 connect to the source terminal of the n-type transistor Q3. Cathodes of each Zener diodes 72 connect to the gate terminal of the n-type transistor Q3. The three Zener diodes 72 and the resistance 73 are implemented as a shunt connection. An end of the resistance 73 connects to the source terminal of the n-type transistor Q3. Another end of the resistance 73 connects to the gate terminal of the n-type transistor Q3.

The upper half protection circuit 81 comprises a p-type transistor Q7, an n-type transistor Q8, an n-type transistor Q9, and the constant voltage terminal Vc. The p-type transistor Q7 and the n-type transistor Q8 are complementary. A gate terminal of the p-type transistor Q7 connects to a gate terminal of the n-type transistor Q8, wherein both the gate terminals connects to the signal input terminal IN_P. A drain terminal of the p-type transistor Q7 connects to a drain terminal of the n-type transistor Q8. A source terminal of the p-type transistor Q7 connects to the constant voltage terminal Vc. A source terminal of the n-type transistor Q8 is grounded. An output terminal of the complementary pair, the p-type transistor Q7 and the n-type transistor Q8, connects to a gate terminal of the n-type transistor Q9. That is, the gate terminal of the n-type transistor Q9 connects to both the drain terminal of the p-type transistor Q7 and the drain terminal of the n-type transistor Q8. A source terminal of the n-type transistor Q9 is grounded. A drain terminal of the n-type transistor Q9 connects to the node 47.

The lower half protection circuit 91 comprises a p-type transistor Q10, a Zener diode 92, resistances 93, 94, and 95, a p-type transistor Q11, and the constant voltage terminal Vc. A gate terminal of the p-type transistor Q10 connects to the signal input terminal IN_N. A drain terminal of the p-type transistor Q10 connects to the resistance 94, a cathode of the Zener diode 92, and a gate terminal of the p-type transistor Q11. The resistance 94 and the Zener diode 92 are implemented as a shunt connection. An anode of the Zener diode 92 connects to the constant voltage terminal Vc. A cathode of the Zener diode 92 connects to the gate terminal of the p-type transistor Q11. A drain terminal of the p-type transistor Q11 connects to the node 49. A source terminal of the p-type transistor Q11 connects to the resistance 95. Another end of the resistance 95 is grounded. In this embodiment, the load 46 represents a transducer or other external equipment. The load 46 is not limited to this embodiment.

Specially, at the state of positive half wave, by using the shunt connection of the Zener diodes 52 and the resistance 53, which bridges across the source terminal and the gate terminal of the p-type transistor Q2, a voltage difference between the gate terminal and the source terminal of the p-type transistor Q2 is maintained within an absolute value. The absolute value is equivalence with an operating voltage range at a reverse bias of the Zener diodes 52. As such, the absolute value presents a dynamic voltage difference, wherein the absolute value ranges from a breakdown voltage of the reverse bias to 0V. Therefore, the dynamic voltage difference generates a dynamic bias to the gate terminal of the p-type transistor Q2. In addition, a voltage difference between the gate terminal and the source terminal of the p-type transistor Q2 is equal to the voltage difference between the anode and the cathode of the Zener diodes 52. By using a voltage restriction of the Zener diodes 52, the p-type transistor Q2 works at a linear region (a triode region) when turning on. The Zener diodes 52 avoid the p-type transistor Q2 work at a breakdown region when turning on. Therefore, the p-type transistor Q2 works at a linear region (a triode region) when turning on. A voltage at the node 48 is close to the first high voltage terminal VH1. At this time, the upper half protection circuit 81 turns off. The lower half protection circuit 91 turns on so that the node 49 is grounded. The lower half protection circuit 91 prevents the n-type transistors Q3 and Q4 from transient over voltage.

Since the node 49 is grounded, a voltage at the gate terminal of the n-type transistors Q3 rapidly becomes $-V_{ZENER}$.

Specially, at the state of negative half wave, by using the shunt connection of the Zener diodes 72 and the resistance 73, which bridges across the gate terminal and the source terminal of the n-type transistor Q3, a voltage difference between the gate terminal and the source terminal of the n-type transistor Q3 is maintained within an absolute value. The absolute value is equivalence with an operating voltage range at a reverse bias of the Zener diodes 72. As such, the absolute value presents a dynamic voltage difference, wherein the absolute value ranges from a breakdown voltage of the reverse bias to 0V. Therefore, the dynamic voltage difference generates a dynamic bias to the gate terminal of the n-type transistor Q3. In addition, a voltage difference between the gate terminal and the source terminal of the n-type transistor Q3 is equal to the voltage difference between the anode and the cathode of the Zener diodes 72. By using a voltage restriction of the Zener diodes 72, the n-type transistor Q3 works at a linear region (a constant current region) when turning on. The Zener diodes 72 avoids the n-type transistor Q3 work at a breakdown region when turning on. Therefore, the n-type transistor Q3 works at a linear region (a triode region) when turning on. A voltage at the node 48 is close to the first low voltage terminal VL1. At this time, the upper half protection circuit 81 turns on so that the node 47 is grounded; and the lower half protection circuit 91 turns off. The upper half protection circuit 81 prevents the p-type transistors Q1 and Q2 from transient over voltage. Since the node 47 is grounded, a voltage at the gate terminal of the p-type transistors Q2 rapidly becomes $+V_{ZENER}$.

The Zener diodes 52 and the resistance 53 restrict the voltage difference between the gate terminal and the source terminal of the p-type transistor Q2. The Zener diodes 72 and the resistance 73 restrict the voltage difference between the gate terminal and the source terminal of the n-type transistor Q3. The p-type transistor Q2 and the n-type transistor Q3 will certainly operate at a linear region when turning on. An output swing of the node 48 is up to VH1~VL1, which is close to a voltage difference between the highest voltage and the lowest voltage of the system. Therefore, this embodiment achieves a large swing of output voltage by using power semiconductor devices having low-voltage tolerance. The large swing of output voltages are provided for high voltage or high power equipment, such as ultrasonic wave transducers or logic inverters.

Figure 4:
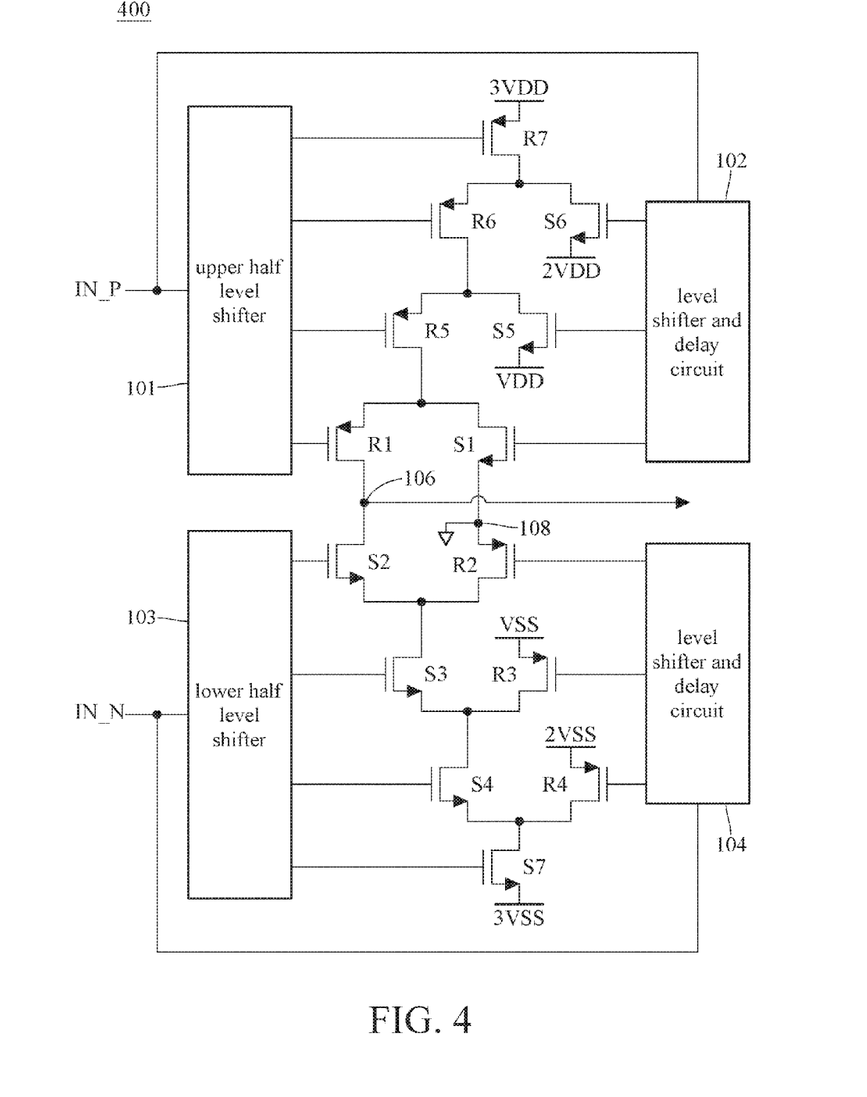
FIG. 4 is a diagram illustrating an output stage circuit in accordance with an embodiment of the present disclosure.

FIG. 4 is a diagram illustrating an output stage circuit 400 in accordance with an embodiment of the present disclosure. The output stage circuit 400 comprises an upper half level shifter 101, a level shifter and delay circuit 102, a lower half level shifter 103, a level shifter and delay circuit 104, p-type transistors R1~R7, and n-type transistors S1~S7. A signal input terminal IN_P connects to the upper half level shifter 101 and the level shifter and delay circuit 102. A signal input terminal IN_N connects to the lower half level shifter 103 and the level shifter and delay circuit 104. Regarding an upper half of the output stage circuit 400, the output stage circuit 400 comprises a plurality of complementary pairs, wherein each complementary pair comprises a p-type transistor and an n-type transistor, for example, a p-type transistor R1 and an n-type transistor S1. In an embodiment, the complementary pairs are performed by transistors, such as complementary metal-oxide-semiconductors (CMOS) or complementary power metal-oxide-semiconductors. A source terminal of the p-type transistor R1 connects to a drain terminal of the n-type transistor S1. A gate terminal of the p-type transistor R1 receives signals coming from the upper half level shifter 101. A gate terminal of the n-type transistor S1 receives signals coming from the level shifter and delay circuit 102. A p-type transistor R5 and an n-type transistor S5 are regarded as another complementary pair. A drain terminal of the p-type transistor R5 connects to a source terminal of the p-type transistor R1 and a drain terminal of the n-type transistor S1. A source terminal of the p-type transistor R5 connects to a drain terminal of the n-type transistor S5. A source terminal of the n-type transistor S5 connects to a voltage terminal VDD. A gate terminal of the p-type transistor R5 receives signals coming from the upper half level shifter 101. A gate terminal of the n-type transistor S5 receives signals coming from the level shifter and delay circuit 102. A p-type transistor R6 and an n-type transistor S6 are regarded as another complementary pair. A drain terminal of the p-type transistor R6 connects to the source terminal of the p-type transistor R5 and the drain terminal of the n-type transistor S5. A source terminal of the p-type transistor R6 connects to a drain terminal of the n-type transistor S6. A source terminal of the n-type transistor S6 connects to a voltage terminal 2VDD, which is two times larger than 1VDD. A gate terminal of the p-type transistor R6 receives signals coming from the upper half level shifter 101. A gate terminal of the n-type transistor S6 receives signals coming from the level shifter and delay circuit 102. A drain terminal of the p-type transistor R7 connects to a source terminal of the p-type transistor R6 and the drain terminal of the n-type transistor S6. A source terminal of the p-type transistor R7 connects to a voltage terminal 3VDD, which is three times larger than 1VDD.

Regarding the lower half of the output stage circuit 400, the output stage circuit 400 comprises a plurality of complementary pairs, wherein each complementary pair comprises a p-type transistor and an n-type transistor, for example, an n-type transistor S2 and a p-type transistor R2. A source terminal of the n-type transistor S2 connects to a drain terminal of the p-type transistor R2. A gate terminal of the n-type transistor S2 receives signals coming from the lower half level shifter 103. A gate terminal of the p-type transistor R2 receives signals coming from the level shifter and delay circuit 104. An n-type transistor S3 and a p-type transistor R3 are regarded as another complementary pair. A drain terminal of the n-type transistor S3 connects to the source terminal of the n-type transistor S2 and the drain terminal of the p-type transistor R2. A source terminal of the n-type transistor S3 connects to a drain terminal of the p-type transistor R3. A source terminal of the p-type transistor R3 connects to a voltage terminal VSS. A gate terminal of the n-type transistor S3 receives signals coming from the lower half level shifter 103. A gate terminal of the p-type transistor R3 receives signals coming from the level shifter and delay circuit 104. An n-type transistor S4 and a p-type transistor R4 are regarded as another complementary pair. A drain terminal of the n-type transistor S4 connects to the source terminal of the n-type transistor S3 and the drain terminal of the p-type transistor R3. A source terminal of the n-type transistor S4 connects to a drain terminal of the p-type transistor R4. A source terminal of the p-type transistor R4 connects to a voltage terminal 2VSS, which is two times larger than 1VSS. A gate terminal of the n-type transistor S4 receives signals coming from the lower half level shifter 103. A gate terminal of the p-type transistor R4 receives signals coming from the level shifter and delay circuit 104. A drain terminal of the n-type transistor S7 connects to the source terminal of the n-type transistor S4 and the drain terminal of the p-type transistor R4. A source terminal of the n-type transistor S7 connects to a voltage terminal 3VSS, which is three times larger than 1VSS.

A node 106 is located between the p-type transistor R1 and the n-type transistor S1. The node 106 connects to the drain terminal of the p-type transistor R1 and the drain terminal of the n-type transistor S2. A node 108 is located between the n-type transistor S1 and the p-type transistor R2. The node 108 connects to the source terminal of the n-type transistor S1 and the source terminal of the p-type transistor R2. In this embodiment, the complementary pairs cascade each other. The output stage circuit 400 is able to be expanded and has more complementary pairs. In accordance with increasing of numbers of the complementary pairs, for example, the upper half portion of the output stage circuit 400 has m complementary pairs and connects to a voltage terminal m VDD. The lower half portion of the output stage circuit 400 has n complementary pairs and connects to a voltage terminal n VSS. In brief, the complementary pairs cascade each other so that an output swing of the output stage circuit 400 becomes wider. The output swing achieves a range from m VDD to n VSS. Therefore, this embodiment achieves a large swing of output voltage by using power semiconductor devices having low-voltage tolerance. The large swing of output voltages are provided for high voltage or high power equipment.

In brief, the present disclosure provides an output stage circuit applicable to analog circuit or digital circuit, which is integrated or discrete. By restriction of the Zener diodes, transistors of power inverters will work at a linear region when turning on. The output stage circuit is not limited to breakdown voltages of each devices or components. The output stage circuit made of power semiconductor devices having low-voltage tolerance achieves a large swing of output voltage. In another case, the output stage circuit achieves multiplication of output voltages by using power semiconductor devices, which are scaled down. This configuration is applicable to medical image systems having high-voltage emitting components, such as emitting circuit of ultrasonic scanners, computerized tomographic scans, and nuclear magnetic resonance imaging. This configuration is also applicable to engineering systems, such as industrial ultrasonic probing, transmitters of communication integrated circuits, or high quality audifiers.

In an embodiment, the at least one Zener diode bridges between the gate terminal and the source terminal of the at least one transistor, and an anode of the at least one Zener diode connects to the gate terminal, a cathode of the at least one Zener diode connects to the source terminal.

In an embodiment, the at least one Zener diode bridges between the gate terminal and the source terminal of the at least one transistor, and an anode of the at least one Zener diode connects to the source terminal, a cathode of the at least one Zener diode connects to the gate terminal.

In an embodiment, the dynamic bias circuit further comprises at least one resistance connected with the at least one Zener diode in parallel.

In an embodiment, the dynamic bias circuit further comprises at least one diode connected between the system voltage terminal and the gate terminal, wherein an anode of the at least one diode connects to the gate terminal, a cathode of the at least one diode connects to the system voltage terminal.

In an embodiment, the dynamic bias circuit further comprises at least one diode connected between the system voltage terminal and the gate terminal, wherein an anode of the at least one diode connects to the system voltage terminal, a cathode of the at least one diode connects to the gate terminal.

In an embodiment, the power inverter comprises at least two pairs of complementary metal-oxide-semiconductors (CMOS) cascaded together.

In an embodiment, the output stage circuit further comprises a protection circuit connected to the power inverter, configured to guide transient over voltage. The protection circuit comprises at least one transistor, wherein a gate terminal of the at least one transistor couples to the signal terminal, a source terminal of the at least one transistor is grounded, a drain terminal of the at least one transistor of the protection circuit connects to the source terminal of the at least one transistor of the power inverter.

In an embodiment, the output stage circuit further comprises a protection circuit connected to the power inverter, configured to guide transient over voltage. The protection circuit comprises at least one transistor, wherein a gate terminal of the at least one transistor couples to the signal terminal, a source terminal of the at least one transistor is grounded, a drain terminal of the at least one transistor of the protection circuit connects to the source terminal of the at least one transistor of the power inverter.

In an embodiment, the output stage circuit further comprises at least one level shifter, wherein the at least one level shifter respectively connects to the signal terminal, the system voltage terminal, and a gate terminal of the power inverter.

In an embodiment, the system voltage comprises a first high voltage terminal, wherein the first high voltage terminal connects to a source terminal of the power inverter; a second high voltage terminal, configured that an output voltage of the second high voltage terminal is higher than an output voltage of the second high voltage terminal, and the output voltages of the first and second high voltage terminals are positive values; a first low voltage terminal, wherein the first low voltage terminal connects to a source terminal of the power inverter; and a second low voltage terminal, configured that an output voltage of the first low voltage terminal is smaller than an output voltage of the second low voltage terminal, wherein the output voltages of the first and second low voltage terminals are negative values.

In an embodiment, the signal processing method of output stage circuit further comprises: turning off a protection circuit of the p-type transistor, and turning on a protection circuit of the n-type transistor in accordance with the first level signal; and turning off the protection circuit of the n-type transistor, and turning on the protection circuit of the p-type transistor in accordance with the second level signal.

It will be apparent to those skilled in the art that various modifications and variations can be made to the disclosed embodiments. It is intended that the specification and examples be considered as exemplars only, with a true scope of the disclosure being indicated by the following claims and their equivalents.

What is claimed is:
1. An output stage circuit, comprising:
a power inverter, coupled to a signal terminal, and comprising at least two pairs of complementary metal-oxide-semiconductors (CMOS) cascaded together; and
a dynamic bias circuit, wherein the dynamic bias circuit connects between a system voltage terminal and the power inverter, the dynamic bias circuit comprises:
at least one Zener diode, configured to maintain a voltage difference between a gate terminal and a source terminal of at least one transistor of the power inverter within a first absolute value range;
configured to maintain a voltage difference between the gate terminal and a drain terminal of the at least one transistor within a second absolute value range; and
configured to maintain a voltage difference between the drain terminal and the source terminal of the at least one transistor within the second absolute value range.

2. The output stage circuit of claim 1, wherein the at least one Zener diode bridges between the gate terminal and the source terminal of the at least one transistor, and an anode of the at least one Zener diode connects to the gate terminal, a cathode of the at least one Zener diode connects to the source terminal.

3. The output stage circuit of claim 1, wherein the at least one Zener diode bridges between the gate terminal and the source terminal of the at least one transistor, and an anode of the at least one Zener diode connects to the source terminal, a cathode of the at least one Zener diode connects to the gate terminal.

4. The output stage circuit of claim 1, wherein the dynamic bias circuit further comprises:
at least one resistance connected with the at least one Zener diode in parallel.

5. The output stage circuit of claim 1, wherein the dynamic bias circuit further comprises:
at least one diode connected between the system voltage terminal and the gate terminal,
wherein an anode of the at least one diode connects to the gate terminal, a cathode of the at least one diode connects to the system voltage terminal.

6. The output stage circuit of claim 1, wherein the dynamic bias circuit further comprises:
another diode connected between the system voltage terminal and the gate terminal,
wherein an anode of said another diode connects to the system voltage terminal, a cathode of said another diode connects to the gate terminal.

7. The output stage circuit of claim 1, further comprises:
a protection circuit connected to the power inverter, configured to guide transient over voltage, the protection circuit comprises:
at least one transistor,
wherein a gate terminal of the at least one transistor couples to the signal terminal, a source terminal of the at least one transistor is grounded, a drain terminal of the at least one transistor of the protection circuit connects to the source terminal of the at least one transistor of the power inverter.

8. The output stage circuit of claim 1, further comprises:
a protection circuit connected to the power inverter, configured to guide transient over voltage, the protection circuit comprises:
at least one transistor,
wherein a gate terminal of the at least one transistor couples to the signal terminal, a source terminal of the at least one transistor is grounded, a drain terminal of the at least one transistor of the protection circuit connects to the source terminal of the at least one transistor of the power inverter.

9. The output stage circuit of claim 1, further comprises:
at least one level shifter,
wherein the at least one level shifter respectively connects to the signal terminal, the system voltage terminal, and a gate terminal of the power inverter.

10. The output stage circuit of claim 1, wherein the system voltage comprises:
a first high voltage terminal, wherein the first high voltage terminal connects to a source terminal of the power inverter;
a second high voltage terminal, configured that an output voltage of the first high voltage terminal is higher than an output voltage of the second high voltage terminal, and the output voltages of the first and second high voltage terminals are positive values;
a first low voltage terminal, wherein the first low voltage terminal connects to a source terminal of the power inverter; and
a second low voltage terminal, configured that an output voltage of the first low voltage terminal is smaller than an output voltage of the second low voltage terminal, wherein the output voltages of the first and second low voltage terminals are negative values.

11. A signal processing method of output stage circuit comprising:
receiving a first level signal;
maintaining a voltage difference between a gate terminal and a source terminal of a p-type transistor, wherein the voltage difference enables the p-type transistor to work at a linear region when turning on;
outputting a highest system voltage;
receiving a second level signal;
maintaining a voltage difference between a gate terminal and a source terminal of an n-type transistor, wherein the voltage difference enables the n-type transistor to work at a linear region when turning on; and
outputting a lowest system voltage.

12. The signal processing method of output stage circuit of claim 11, further comprises:
turning off a protection circuit of the p-type transistor, and turning on a protection circuit of the n-type transistor in accordance with the first level signal; and
turning off the protection circuit of the n-type transistor, and turning on the protection circuit of the p-type transistor in accordance with the second level signal.

* * * * *